United States Patent
Kolosov et al.

(10) Patent No.: US 9,082,587 B2
(45) Date of Patent: Jul. 14, 2015

(54) METHOD AND APPARATUS FOR ION BEAM POLISHING

(75) Inventors: Oleg Victor Kolosov, Lancaster (GB); Ilja Grishin, Lancaster (GB)

(73) Assignee: Lancaster University Business Enterprises Limited (GB)

( * ) Notice: Subject to any disclaimer, the term of this patent is extended or adjusted under 35 U.S.C. 154(b) by 344 days.

(21) Appl. No.: 13/586,011

(22) Filed: Aug. 15, 2012

(65) Prior Publication Data

US 2013/0008779 A1 Jan. 10, 2013

Related U.S. Application Data

(63) Continuation of application No. PCT/GB2011/000169, filed on Feb. 10, 2011.

(30) Foreign Application Priority Data

Feb. 17, 2010 (GB) .................................. 1002645.8

(51) Int. Cl.
| | |
|---|---|
| *C23C 14/46* | (2006.01) |
| *H01J 37/305* | (2006.01) |
| *G01N 1/32* | (2006.01) |

(52) U.S. Cl.
CPC .............. *H01J 37/3053* (2013.01); *G01N 1/32* (2013.01); *H01J 2237/20* (2013.01)

(58) Field of Classification Search
USPC ............. 204/192.34, 192.35, 298.32, 298.31, 204/298.36
See application file for complete search history.

(56) References Cited

U.S. PATENT DOCUMENTS

| | | | |
|---|---|---|---|
| 4,326,936 A * | 4/1982 | Jones ....................... | 204/192.34 |
| 4,869,780 A * | 9/1989 | Yang et al. ............... | 204/192.34 |
| 5,472,566 A | 12/1995 | Swann et al. | |
| 5,907,157 A | 5/1999 | Yoshioka et al. | |
| 5,986,264 A | 11/1999 | Gruenewald | |
| 2004/0185586 A1 | 9/2004 | Yasutake et al. | |
| 2005/0081997 A1 | 4/2005 | Yoshioka et al. | |

(Continued)

FOREIGN PATENT DOCUMENTS

| | | |
|---|---|---|
| DE | 41 12 375 A1 | 10/1992 |
| DE | 196 08 082 A1 | 10/1996 |

(Continued)

OTHER PUBLICATIONS

International Search Report and Written Opinion of the International Searching Authority, PCT/GB2011/000169, mailed Jun. 24, 2011.

(Continued)

*Primary Examiner* — Jason M Berman
(74) *Attorney, Agent, or Firm* — Bose McKinney & Evans LLP

(57) ABSTRACT

A method for forming a polished facet between an edge and a face of a sample, involves removing a first portion of the sample by directing an ion beam onto the edge adjacent the first portion along an ion beam axis to leave the polished facet. The ion beam axis lies on an ion beam plane oriented at a glancing incident angle, preferably from 1° to 30°, to a sample plane defined by and parallel to the first face. The ion beam is directed to flow from the edge towards the first face. Also disclosed is a sample preparation apparatus comprising a chamber adapted for evacuation with a sample holder adapted to hold a sample comprising a first face bounded by an edge, and an ion gun arranged to direct an ion beam along an ion beam axis towards the sample.

20 Claims, 4 Drawing Sheets

(56) References Cited

U.S. PATENT DOCUMENTS

| | | |
|---|---|---|
| 2005/0118065 A1 | 6/2005 | Hasegawa et al. |
| 2005/0236587 A1 | 10/2005 | Kodama et al. |
| 2006/0097166 A1 | 5/2006 | Ishitani et al. |
| 2006/0113496 A1 * | 6/2006 | Yoshioka ............... 250/492.21 |
| 2007/0187597 A1 | 8/2007 | Suzuki et al. |
| 2008/0099695 A1 | 5/2008 | Sugizaki |
| 2010/0025577 A1 | 2/2010 | Grunewald et al. |

FOREIGN PATENT DOCUMENTS

| | | | |
|---|---|---|---|
| EP | 0 626 721 | A1 | 11/1994 |
| EP | 1 870 691 | A2 | 12/2007 |
| JP | 2001077058 | A * | 3/2001 |
| JP | 2006-084484 | A | 3/2006 |
| JP | 2007-248368 | A | 9/2007 |
| JP | 2009109236 | A | 5/2009 |
| WO | WO 2004/013661 | A2 | 2/2004 |
| WO | WO 2004/013661 | A3 | 2/2004 |

OTHER PUBLICATIONS

Search Report of UK Intellectual Property Office, GB 1002645.8, dated Nov. 22, 2010.

* cited by examiner

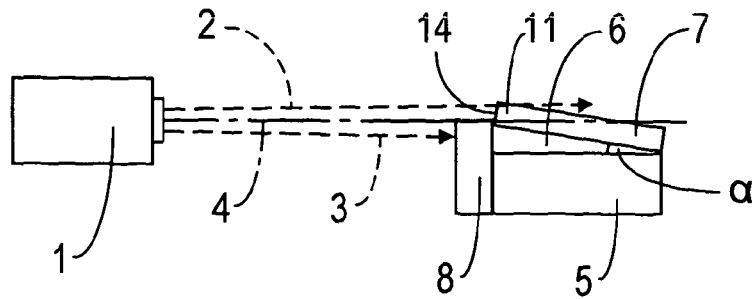
_Fig. 3_
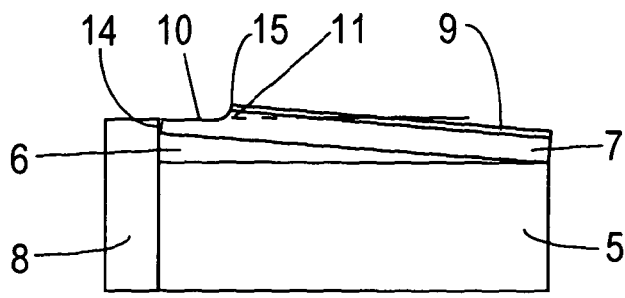
_Fig. 4_
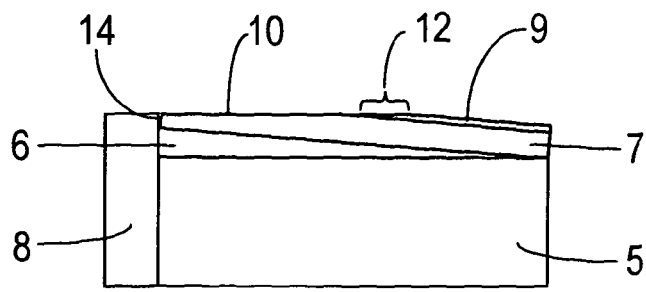
_Fig. 5_
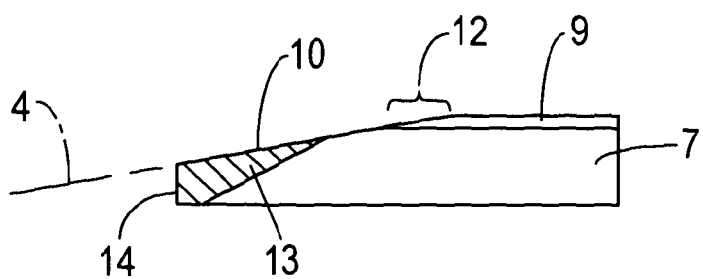
_Fig. 6_

METHOD AND APPARATUS FOR ION BEAM POLISHING

CROSS REFERENCE TO RELATED APPLICATIONS

This is a continuation of International Application PCT/GB2011/000169, with an international filing date of Feb. 10, 2011, and which claims priority from GB 1002645.8 filed on Feb. 17, 2010, and the disclosures of both of these applications from which priority is claimed are incorporated herein by reference.

FIELD

The present invention relates to apparatus and methods for the preparation of samples having polished surfaces or facets suitable for the application of high resolution microscopy techniques such as electron microscopy, scanning probe microscopy and the like. In particular it relates to apparatus and methods for forming highly flat and smooth cross-sections through device structures immediately adjoining a sample surface, to allow high resolution analysis of such device structures. For instance the invention relates to formation of facets on samples having epitaxial layers, multilayer structures, semiconductor thin films and the like where the structures and layers have sub-micrometer scale dimensions. When studying such device structures, it is desirable to achieve polished surfaces or facets with a roughness of the order of 1 nm (root mean square peak-to-trough height) or better.

BACKGROUND

Typically, device structures are formed on one face of a substrate such as a semiconductor wafer. The substrate may typically be a flat tabular body such as a flat disc with opposed faces bounded by an edge or edges.

In order to observe the device structures on such a substrate, it is possible to cleave or cut through the sample to provide a cross-sectional facet, typically at right angles to the opposed faces of the sample. Mechanical cutting and polishing leaves marks and striations which are on too large a scale for techniques such as scanning probe microscopy to be effective. Cleavage may be successful for mono-crystalline structures, but may result in ladder faulting for hetero-structures, again leading to problems when carrying out scanning probe microscopy.

Ion beam polishers are known in the prior art. U.S. Pat. No. 5,907,157 and US2005/0081997A1 disclose methods and apparatus for preparing samples for electron microscopy where an edge of a sample is milled by ion beam milling to give a smooth cross-sectional profile. A mask is used to define a boundary between irradiated and un-irradiated regions and the mask is positioned over a face of the sample so that the polished edge formed by the ion beam removing a portion of the sample is at right angles to the face upon which the mask rests.

Such an arrangement is shown in FIG. 1 of the present specification and will be described in more detail hereinafter.

One problem with such a prior art arrangement is that the ion beam inevitably damages the leading part of the polished facet resulting from ion beam milling (i.e. the part of the facet upon which the ion beam first impinges). This arises from scattering of ions around the mask edge and possibly their partial implantation into the sample. Moreover, it has now been found that the ion beam may create a bevel or round-nosed profile at the leading part of the ion-beam milled edge. Such a bevel may typically extend for several micrometers. This bevel precludes high resolution investigation of surface layers of interest that are in the region adjacent to the surface. In particular, when surface probe microscopy is subsequently carried out, severe scanning problems may result.

Although this problem may be overcome in part by turning the sample over, and using the back of the substrate as the leading part for ion beam milling, it will be necessary to remove considerably more sample in order to polish the device layers on the trailing part of the edge. This may require a considerable length of time and may result in the need to frequently replace sample holders and masks. Furthermore, the area of interest of sub-micrometer dimensions will also be close to the 90 degrees edge. This may lead to the creation of unbalanced forces on the scanning microscope and is known to deteriorate images, especially for images generated in the ambient environment where a water meniscus between the probe and the sample might be present.

Hence there is a need for apparatus and methods which address some or all of the problems in the prior art as set out above.

SUMMARY

One advantage of some embodiments of the present invention, amongst others, is to provide apparatus and methods for providing a polished facet on a sample, adjacent to the sample surface, which exhibits very low surface roughness. It is also an advantage of some embodiments of the invention that the polished facet should be substantially flat rather than exhibiting rounded or beveled edges, and that the polished facet should not be subject to substantial structural damage. It is also an advantage of some embodiments of the invention to provide methods and apparatus which are capable of producing the desired polished facets in a time effective manner without excessive need to replace sample holders and ion beam shields or masks.

It is a further advantage of some embodiments of the invention to provide methods for carrying out scanning probe microscopy on polished facets of samples. It is also an advantage of some embodiments of the invention to achieve high performance scanning probe microscopy investigation, by the polished facet meeting the unpolished sample surface at a glancing angle so that the angle between the polished facet and the unpolished surface, measured inside the sample, is marginally less than 180°. It is a further advantage of some embodiments of the invention to provide a method and apparatus which allows for improved resolution of features present in a cross sectional profile of a sample.

Hence a first aspect of the invention provides a method for forming a polished facet between an edge and a first face of a sample, the sample comprising a first face bounded by the edge, the method comprising removing a first portion of the sample by directing one or more ion beams onto the edge adjacent the first portion along an ion beam axis to leave the polished facet, wherein the ion beam axis lies on an ion beam plane oriented at a glancing incident angle, preferably from 1° to 30°, to a sample plane defined by and parallel to the first face, and wherein the ion beam is directed to flow from the edge towards the first face.

A second aspect of the invention provides a method for carrying out scanning probe microscopy on a polished facet of a sample, wherein the polished facet is produced by a method according to the first aspect of the invention.

A third aspect of the invention provides a sample preparation apparatus comprising: a chamber adapted for evacuation comprising therein a sample holder adapted to hold a sample comprising a first bounded by an edge, and one or more ion guns arranged to direct an ion beam along an ion beam axis towards said sample, wherein the sample holder is configurable to position the sample relative to the ion beam such that a first portion of said sample is removable by the ion beam to leave a polished facet between said edge and said first face of said sample, characterised in that the sample holder is configured to hold said sample whereby the ion beam axis lies on an ion beam plane oriented at a glancing incident angle, such as from 1° to 30°, to a sample plane defined by and parallel to the first face of said sample, and in that the ion beam is arranged to flow from said edge towards said first face.

Other aspects of the invention provide for a method of carrying out scanning electron microscopy on a polished facet of a sample, wherein the polished facet is produced by the method of the first aspect of the invention, scanning probe microscopy (e.g., atomic force microscopy, ultrasonic force microscopy, etc.) and a method for carrying out localized probing of properties (e.g., local probing of electrical transport, nano-indentation probing, etc.) on a polished facet of a sample, wherein the polished facet is produced by the method of the first aspect of the invention.

The first aspect of the invention provides a method for forming a polished facet on a sample. The sample has a first face bounded by an edge, and may typically have first and second opposed faces bounded by an edge. By the term edge is also included "edges". For instance if the sample is a disc, there will be one continuous edge, but if the sample is a square tablet, there will be four edges.

The method of the first aspect comprises removing a first portion of the sample by directing an ion beam onto the edge adjacent the first portion along an ion beam axis in order to leave the polished facet, once the first portion of sample has been removed (eroded away) by the ion beam.

The ion beam will suitably be a collimated ion beam directed along and defining at its central axis an ion beam axis. The ion beam may be substantially parallel to the ion beam axis, but may be slightly divergent or convergent, for instance by up to +/−10° relative to the ion beam axis. Ion guns for generating ion beams, and methods of collimation are well known in the art and will not be detailed further here. A suitable ion beam voltage is 1 to 7 kV, with the ion beam having a diameter or extent of about 200 μm or less. To prevent scattering of the ion beam, the sample and ion beam will be located inside an evacuated chamber with a low gas pressure therein. Typically the method will be operated under high vacuum conditions within the chamber.

The ion beam axis lies on an ion beam plane oriented at a glancing incident angle to a sample plane defined by and parallel to the first face of the sample. Preferably, the glancing angle is from 1° to 30°, more preferably from 2 to 20°, even more preferably from 5 to 10°. The ion beam is directed to flow from the edge towards the first face, which means that in a typical configuration, with a sample mounted so that its first face lies upwards, the ion beam will be directed towards the back of the first face, from below the first face, through the edge of the sample, so that the ion beam would hit the back of the first face were it not for the presence of the first portion of the sample which will be eventually removed by the ion beam to yield the polished facet.

The ion beam may be positioned and have a shape such that it is suitable for removing the first portion to form the polished facet. However, preferably a shield or mask is positioned, between the ion gun and the edge, to define a second portion of the sample shielded from the ion beam, and the first portion unshielded from the ion beam. The shield will shadow the ion beam and prevent it from falling on the second portion of the sample. The shield edge or boundary, defining the shadow, is typically positioned close to the first face of the sample, for instance at a distance from 5 to 100 μm and preferably from 10 to 20 μm from the first face. By this means, a sharp, well defined facet may be formed. The shield is suitably of a material highly resistant to erosion by the ion beam. For instance, the shield may be of a Cobalt Nickel Alloy such as Super Invar®, which has a particularly low coefficient of thermal expansion and so will reduce errors in positioning caused by thermal expansion of the shield as the ion beam impingement on the shield leads to local heating. Other materials, such as sapphire, molybdenum, or tungsten may be suitable as a shield. Typically, the shield edge defining the boundary between the first and second portions of the sample will lie on the ion beam axis. Suitably, the shield will be positioned immediately adjacent to the edge of the sample, preferably abutting the edge of the sample, (this may require milling or lapping the shield or lapping and polishing the sample to the appropriate angle so that the sample and shield may mutually abut), whereby scattering or diffraction of the ion beam around the edge is reduced.

In addition to producing a highly smooth, flat polished facet, the method of the invention also yields effective magnification of the features present in the cross-sectional profile of the sample. An epitaxial layer which would be 10 nm thick in a conventional cross section taken at 90° to the first face would have a thickness of $10/\sin(5°)=115$ nm measured along the polished facet for a glancing angle of 5°.

The method of the first aspect of the invention may comprise monitoring of removal of the first portion whereby an extent of removal may be determined. Microscopic monitoring may be used, for instance an optical microscope may be used, directed onto the sample, or electron microscopy methods may be suitable, such as scanning electron microscopy, for instance.

A parameter for the ion beam may be varied as a function of the extent of removal of the first portion as the ion beam removal of the first portion progresses. This extent of removal may be monitored by means of microscopy as set out above. Image analysis apparatus, for instance connected to a microscope, may be used in order to generate a signal related to the extent of removal, and such a signal may be used as input to a control means operably connected to the ion gun. The control means may comprise a computer program operating on a computer means such as a microprocessor or the like, with the computer program arranged to vary the ion beam parameters in response to a signal from the image analysis apparatus. Alternatively, for instance, an observer may assess the progress of the removal and manually control the ion beam parameters.

Further details of monitoring and control means are set out below in relation to the apparatus of the invention suitable for use with the methods of the invention, and these may be particularly useful in the later stages of the removal process of the first portion. For instance, such control may be valuable once the polished facet reaches the first face and impinging ions from the ion beam commence sputtering the area of the first face adjacent to the polished facet in transmission. Suitable monitoring or detection means, generating signals for operably controlling process parameters for the ion beam (such as reducing intensity of the ion beam or changing its position or geometry) may be used to preserve the fine geometry of the polished facet edge with the first face. This edge may be required as the subject of subsequent detailed analysis.

The ion beam voltage may, for instance, be reduced from an initial voltage to a final voltage prior to completion of removal of the first portion. This may permit rapid removal of the first portion initially, with lower voltages in operation (hence lower velocity ions) as the last part of the first portion is removed. This may be used to give a reduction in ion damage for the part of the polished facet which is of most interest for subsequent analysis.

For similar reasons, the ion beam current may correspondingly be reduced from an initial current to a final current prior to completion of removal of the first portion.

Additionally, or alternatively, offsetting of the ion beam, prior to the completion of the removal of the first portion, may be used to further improve the geometry of the polished facet edge in the region adjacent to the first face. By displacing either the ion gun, or the mask, or the sample in its sample holder, or the ion beam, or any combination of these, in such a manner that the first portion moves closer to the upper periphery of the ion beam, then the angular distribution of the ions polishing the first portion may be adjusted to provide a reduced glancing angle with respect to the first portion. This change may be used to reduce the effective length of the collision cascades initiated by the impinging ions which allows the polishing of the facet to proceed with reduction in damage to the first face. Such displacement may preferably be effected during the removal of the first portion without need for stopping the removal process and without needing to vent the chamber so that the overall process time is minimized and the life of the ion source is not reduced by unnecessary exposure to air. For instance, the displacement may be achieved by means of motorized displacement of the holder, mask or ion source (controlled manually or by a computer program). In another suitable arrangement, the ion beam may be displaced by means of an electromagnetic field.

Suitably, the sample may be yawed (i.e. rotated a few degrees, such as +/−20° or less) to and fro, about an axis normal to the ion beam plane whilst the first portion is being removed. This may lead to a reduction in build-up of striations along the polished facet parallel to the ion beam axis.

As an alternative to moving the sample, greater precision may ensue from the ion beam axis being moved from side to side whilst remaining directed along the ion beam plane whilst the first portion is being removed. For instance the ion beam axis may be moved by means of a time-varying electromagnetic field, such as a magnetic field applied by coils or moveable permanent magnet or a time-varying electric field applied between charged parallel plates through which the ion beam may pass.

Two or more ion beams may be directed along the ion beam plane to substantially converge at the first portion. For instance three ion beams may be directed towards the first portion. Once again, this may assist in avoidance of striations and will speed up the formation of the polished facet. The features set out for the ion beam above may be applied to each additional ion beam.

Typically, the sample may be a device substrate comprising one or more layers at the first face. The ion beam may be any suitable ion beam, preferably a noble gas ion beam, more preferably an argon ion beam.

The edge at the first portion of the sample may be milled (e.g., mechanically milled or polished) to form an angle of 90° minus the incident angle with the first face prior to removal of the first portion. This may enable the milled edge to be positioned to abut the shield when the method is put into effect as the first portion is removed.

The second aspect of the invention provides a method for carrying out scanning probe microscopy on a polished facet of a sample, wherein the polished facet is produced by a method according to the first aspect of the invention. The features of the first aspect as set out above are also applicable to the second aspect. The flatness and smoothness of the polished facet arising from the method of the invention, along with the magnification of features in the widened cross sectional profile arising from the method, make it particularly applicable to Scanning probe microscopy techniques such as atomic force microscopy (AFM), scanning tunneling microscopy (STM) and ultrasonic force microscopy (UFM). Other variants of these microscopy techniques, where an image of the surface is obtained by mechanically moving the probe in a raster scan of the specimen, for instance in boustrophedon or raster manner, and recording the probe-surface interaction as a function of position.

A third aspect of the invention provides a sample preparation apparatus. This comprises a chamber adapted for evacuation comprising therein a sample holder adapted to hold a sample comprising a first face bounded by an edge, and an ion gun arranged to direct an ion beam along an ion beam axis towards said sample. The sample holder is configurable to position the sample relative to the ion beam such that a first portion of said sample is removable by the ion beam to leave a polished facet between said edge and said first face of said sample. The sample holder is configured to hold said sample whereby the ion beam axis lies on an ion beam plane oriented at a glancing incident angle, preferably from 1° to 30°, to a sample plane defined by and parallel to the first face of said sample, and in that the ion beam is arranged to flow from said edge towards said first face.

The apparatus of the third aspect of the invention is for putting into effect the method of the first aspect of the invention, and the features set out above in relation to that first aspect are applicable to the third aspect, and vice versa.

The apparatus may further comprise a shield positioned between the ion gun and the sample holder to define said first portion of said sample unshielded from the ion beam and a second portion of said sample shielded from the ion beam.

The apparatus may comprise a means for monitoring the sample removal process.

The means for monitoring the sample removal process may be adapted to provide signals related to the extent of removal of said first portion.

For instance, the means for monitoring the sample removal process may comprise or consist of a microscope means arranged or arrangeable to monitor the sample during removal of said first portion. Other means for monitoring may include an optical arrangement for the detection of changes in light reflectance from the polished facet arising from progress of removal of the first portion. An example of such is an arrangement would be a collimated light source directed at the facet with a camera such as a CCD (charge coupled device) camera used for detection.

The apparatus may comprise a control means operably connected to the ion gun and to the means for monitoring the sample removal process and adapted to vary one or more parameters of the ion beam during removal of said first portion in response to the signals related to the extent of removal of the first portion received from the means for monitoring the sample removal process according to a control program. The control program will typically be a computer program running on a microprocessor or other suitable computing means or logic gate array operably connected to the apparatus.

The apparatus comprises a means for varying the ion beam position relative to said sample in response to the signals from the means for monitoring, related to the extent of removal of the first portion. For instance, the sample holder may be fitted with a position adjustment means, or the ion gun may be provided with a means for adjusting its position.

The apparatus may comprise a means for varying the ion beam geometry in response to the signals from the means for monitoring, related to the extent of removal of the first portion. In other words, the shape of the beam may be adjustable.

The ion gun may comprise a mechanical adjustment means whereby the position and/or geometry of the ion beam are variable in response to the signals from the means for monitoring, related to the extent of removal of the first portion.

In an alternate arrangement, the ion gun may comprise an electromagnetic adjustment means whereby the position and/or geometry of the ion beam are variable in response to the signals from the means for monitoring, related to the extent of removal of the first portion.

A microscope means may be arranged to monitor the sample during removal of said first portion. The microscope means may be adapted to provide signals related to the extent of removal of said first portion.

The apparatus may further comprise a control means operably connected to the ion gun and to the microscope means and adapted to vary parameters of the ion beam during removal of said first portion in response to the signals received from the microscope means according to a control program. The advantages for this are as set out hereinbefore.

Inspection of cross-sections of device structures at surfaces of substrates is important during the development and prototyping of miniature devices, and also for sampling production quality. Fields where the present invention may be applied include, without limitation, semiconductor devices, thin-film structures, epitaxial structures, nano-machines and hybrid devices. Some subtopics include, without limitation, VLSI (very large scale integration), optoelectronics, semiconductor lasers, light-emitting diodes, quantum electronics, silicon-on-insulator devices, microfluidics, etc.

BRIEF DESCRIPTION OF THE DRAWINGS

Specific embodiments of the present invention will now be described, by way of example only, with reference to the accompanying drawings in which:

FIG. 3 shows a schematic side view of a first embodiment according to the invention, FIG. 4 shows a detailed side view of the sample holder and shield of the first embodiment, with a sample having a polished facet partially completed using the method of the invention, FIG. 5 shows a detailed side view of the sample holder and shield of the first embodiment, with a sample having a polished facet prepared according to the invention, FIG. 6 shows a cross-sectional side view of a sample having the polished facet prepared by the method of the invention using the first embodiment.

DETAILED DESCRIPTION

Figure 1:
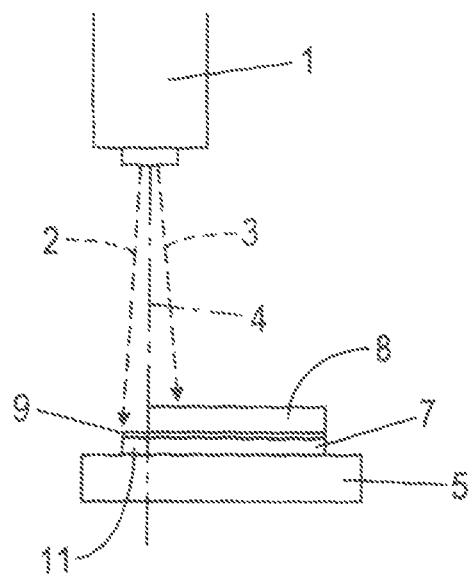
FIG. 1 shows a schematic side view of a prior art ion beam milling apparatus.

In the prior art arrangement, shown in FIG. 1, an ion gun 1 is arranged to direct an ion beam having an extent defined by beam edges 2, 3 along an ion beam axis 4 towards a sample 7 having a device layer 9 on its upper first face. The sample is positioned with its lower second face on a sample holder 5. A shield 8 sits on the first face. The shield 8 shields most of the sample 7 from the ion beam, leaving a first portion 11 unshielded. It is this first portion 11 that is to be removed by the ion beam. The ion beam axis 4 is substantially normal to the first face and device layer 9 of the sample 7.

Figure 2:
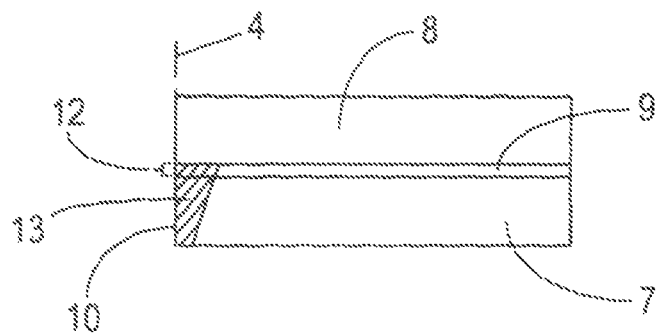
FIG. 2 shows a schematic cross section through a sample milled using the prior art apparatus of FIG. 1 with the shield still in place.

FIG. 2 shows cross-sectional detail of the sample 7 and mask 8 of FIG. 1 after removal of the first portion 11 by the ion beam directed along ion beam axis 4. A polished facet 10 has been formed for the body of the sample 7 with a portion 12 of polished facet 10 corresponding to the cross sectional profile of device layer 9. The shaded region 13 indicates the extent of damage to the sample arising from implantation of ions from the ion beam.

FIG. 3 shows an arrangement according to the first embodiment of the invention with an ion gun 1 arranged to direct an ion beam having an extent defined by beam edges 2, 3, along an ion beam axis 4 towards a sample 7 having a device layer 9 on its upper first face. The sample is positioned with its lower second face on a wedge 6 positioned on sample holder 5 so that the sample lies at an angle α (α is about 5° in the embodiment shown) to the horizontal. The ion beam axis is substantially horizontal and is directed towards an edge 14 of the sample, so that the ion beam axis forms a glancing angle α with the first face and device layer 9 of the sample 7.

A shield 8 is placed in front of the edge 1 and the top edged of the shield 8 defines a boundary between the first portion 11 of sample 7 to be removed by the ion beam and the remainder of the sample 7.

Turning to FIGS. 4 and 5, these show the sample 7, sample holder 5, shield 8 and wedge 6 in more detail as the removal of first portion 11 progresses from partial removal in FIG. 4 to complete removal to leave the polished facet 10 in FIG. 5.

It can be seen in FIG. 4 that there is a distinct boundary 15 between the partially complete polished facet 10 and the first portion to be removed 11 which remains. In FIG. 5 the entire first portion 11 has been removed by the ion beam.

Turning to FIG. 6, this shows a cross-sectional view through the sample from FIG. 5. The original direction of the ion beam axis 4 is also indicated in FIG. 6. Because the ion beam first encounters the edge 14 before continuing on to remove the first portion 11, the region damaged by ion implantation 13, does not extend as far as the portion of polished facet 12 corresponding to the device layer 9. Furthermore, it can be seen that the portion 12 is of considerably greater width than the corresponding portion 12 arising from the prior art method of FIG. 1. This is in spite of the device layer 9 having the same thickness in each case.

Figure 7:
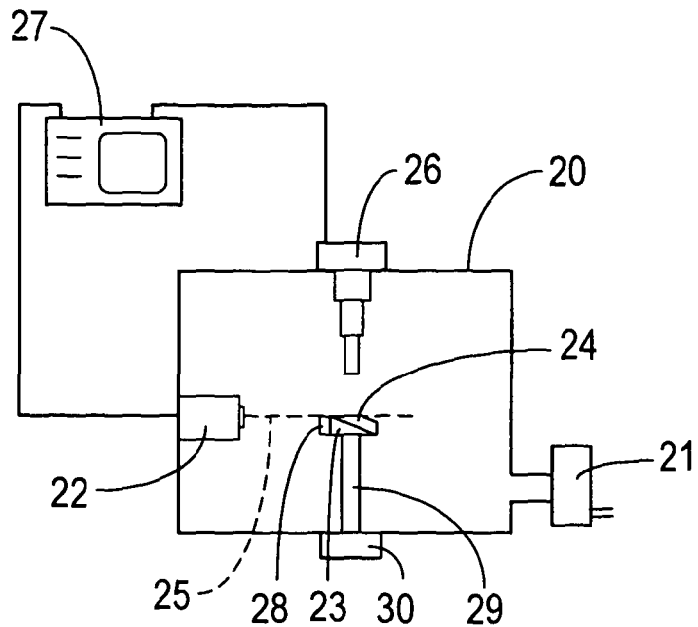
FIG. 7 shows a schematic cross-sectional view of an embodiment of a sample preparation apparatus according to the invention.
Figure 8:
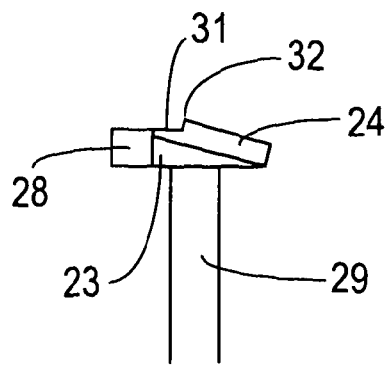
FIG. 8 shows a detailed side view of the sample holder arrangement of the embodiment of FIG. 7.

FIG. 7 shows a schematic cross sectional view of an embodiment of a sample preparation apparatus according to the invention. FIG. 8 shows detail of the sample holder. The chamber 20 is arranged for evacuation by a pumping means 21. An entrance hatch (not shown) allows samples to be positioned in the chamber. A sample holder 23 on a rod 29 supports a sample 24 positioned in an ion beam 25 from an ion gun 22. A shield 28 masks a second portion of the sample 24 from the ion beam 25 leaving a first portion to be removed by the ion beam to leave a polished facet 31. The rod 23 is rotatable about its long axis by a motor 30. A microscope apparatus 26 is positioned to form an image signal of the sample's first face as the first portion is removed by the ion beam 25 to produce the polished facet 31 leaving a visible boundary 32 which moves across the first face of sample 24, disappearing once the removal of the first portion is complete. A control means 27 in the form of a microcomputer running a control program monitors the image signal sent from the microscope apparatus 26 and modifies the voltage and current of the ion beam as the progress of removal is monitored by observation of boundary 32, reducing one or both of the voltage and current of the ion beam as the removal of the first portion nears completion. By this means, risk of ion beam damage, to the polished facet section closest to the first face of the sample 24 is reduced without significant increase in the total time needed for completion of the operation. Low beam voltage/current would lead to longer total removal times if used for the entire removal process, but by dropping the beam intensity only at the last stage, the additional time needed is acceptable. The sample holder 23 may be yawed (i.e. rotated cyclically) about the long axis of rod 23 whilst ion beam milling is underway in order to reduce formation of striations on the polished facet being formed.

Figure 9:
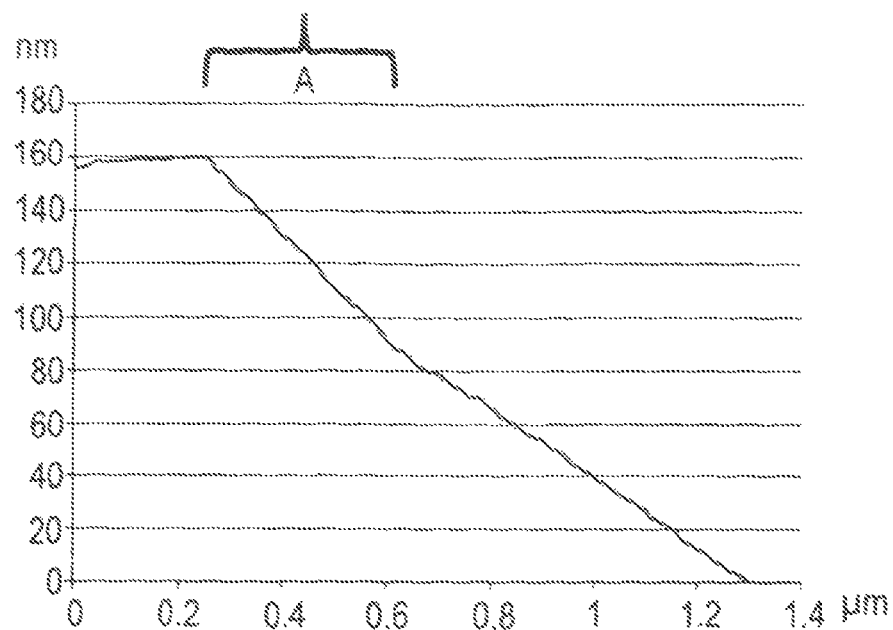
FIG. 9 shows a topographical profile of the sample having polished facet adjacent to the sample surface prepared by the method of the invention using the first embodiment of FIGS. 3 to 6.

Turning to FIG. 9, this shows a graph indicating the topography of the surface of a facet as prepared by the first embodiment of FIGS. 3 to 6. The surface profile has been measured using AFM (atomic force microscopy) revealing a smooth flat profile for the facet produced by the method of the invention. The ordinate on the graph is the distance in micrometers from the commencement of probe contact and the abscissa shows surface height in nm. The region A is where the polished facet meets the unpolished, shielded portion of the surface of the sample. It can be seen that a geometrically flat shape results from the method of the invention.

Figure 10:
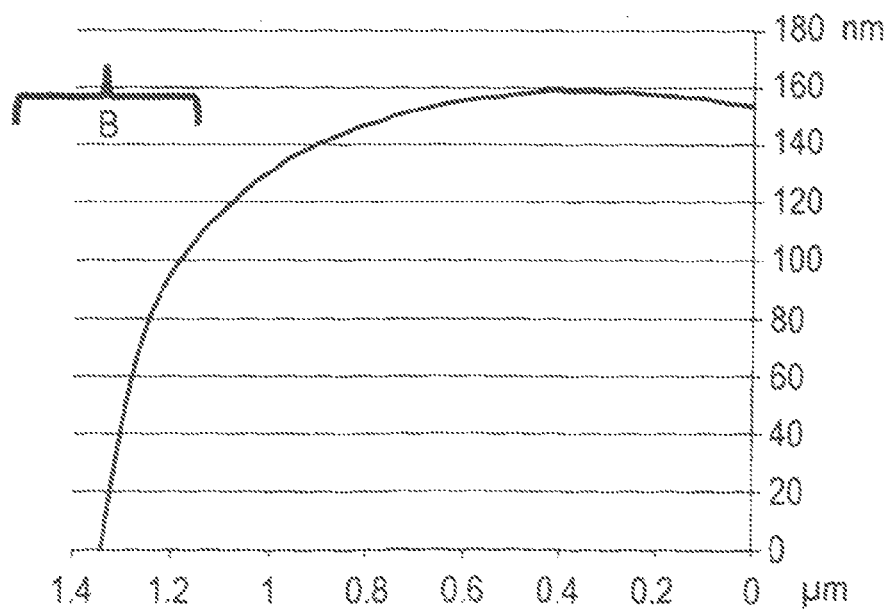
FIG. 10 shows a topographical profile of the sample having polished facet adjacent to the sample surface prepared by the prior-art embodiment of FIGS. 1 and 2.

FIG. 10 shows an AFM profile across a facet generated by the prior art method as set out in FIGS. 1 and 2. In this case, AFM scanning has to proceed in the opposite direction (towards the edge between facet and surface) because of the large beveled region generated adjacent to the unpolished, shielded surface. Because of this, the ordinate of the graph has been plotted in the opposite direction so that for both FIGS. 9 and 10, the unpolished surface of the sample corresponds to the left of the figure. This is indicated by the region B in FIG. 10. For the prior art method of forming the cross-section, the region of most interest, immediately adjacent to the unpolished surface, is not accessible to the AFM measurement technique because of the bevel arising from the prior art polishing method.

It will be appreciated that numerous modifications to the above described embodiment may be made without departing from the scope of the invention as defined in the appended claims. For example, the microscope means 26 may be an electron microscope or focused laser beam with the CCD detector for reflected and scattered beam by the sample. Rather than using a wedge 6 to set the angle α of the sample relative to the ion beam axis 4, the sample holder 5, 23 may include a tilting table configurable to select a required angle α. In addition to the use of the method and apparatus for sample preparation for subsequent investigation, the method and apparatus of the invention may also be used for the preparation of highly polished facets on devices such as semiconductor lasers, or for the provision of facets suitable for making connections to device layers. The enlargement of the spacing between device layers inherent to the method makes it particularly useful for this purpose.

The described and illustrated embodiments are to be considered as illustrative and not restrictive in character, it being understood that only the preferred embodiments have been shown and described and that all changes and modifications that come within the scope of the inventions as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim.

Throughout this specification, the term "comprising" or "comprises" means including the component(s) specified but not to the exclusion of the presence of others. The term "consisting of", "consisting essentially of" or "consists essentially of" means including the components specified but excluding other components except for materials present as impurities, unavoidable materials present as a result of processes used to provide the components, and components added for a purpose other than achieving the technical effect of the invention.

Whenever appropriate, the use of the term "comprises" or "comprising" may also be taken to include the meaning "consists of" or "consists essentially of".

Aspects of the invention can be implemented in any convenient form. For example where computer programs may be provided to carry out the methods described herein, such computer programs may be carried on appropriate computer readable media, which term includes appropriate tangible storage devices (e.g., discs). Aspects of the invention may also be implemented by way of appropriately programmed computers or programmable logic devices.

The invention claimed is:

1. A method for forming a polished facet between an edge and a first face of a sample, the sample comprising a first face bounded by the edge, and the first face comprising a device layer, the method comprising removing a first portion of the sample by directing an ion beam onto the edge adjacent the first portion along an ion beam axis to form the polished facet and such that ion beam does not impinge onto the exterior of the first face, wherein the ion beam axis lies on an ion beam plane oriented at a glancing incident angle from 1° to 30° to a sample plane defined by and parallel to the first face, and wherein the ion beam is directed to flow from the edge towards the first face in a manner such that ions of the ion beam cross the plane of the first face from a space originally occupied by the sample, to a space unoccupied by the sample above the first face and therefore would impinge on a back of the first face if not for the presence of the first portion of the sample, removed by the ion beam to form the polished facet.

2. The method of claim 1, wherein a shield is positioned between the ion gun and the edge to define a second portion of the sample shielded from the ion beam, and the first portion unshielded from the ion beam.

3. The method of claim 1 comprising monitoring of removal of the first portion whereby an extent of removal may be determined and wherein the ion beam voltage and/or the ion beam current is reduced from an initial voltage to a final voltage prior to completion of removal of the first portion.

4. The method of claim 1 wherein the sample is yawed about an axis normal to the ion beam plane whilst the first portion is being removed.

5. The method of claim 1 wherein the ion beam axis is moved from side to side whilst remaining directed along the ion beam plane whilst the first portion is being removed.

6. The method of claim 1 wherein two or more ion beams are directed along the ion beam plane to substantially converge at the first portion.

7. The method of claim 1 wherein the sample is a device substrate comprising one or more layers at the first face.

8. The method of claim 1 wherein the ion beam is a noble gas ion beam.

9. The method of claim 8 wherein the ion beam is an argon ion beam.

10. The method of claim 1 wherein the edge at the first portion is milled to form an angle of 90° minus the incident angle with the first face prior to removal of the first portion, whereby the milled edge may be positioned to abut the shield as the first portion is removed.

11. The method of claim 1 further comprising carrying out scanning probe microscopy on the polished facet of the sample.

12. The method of claim 1 further comprising carrying out scanning electron microscopy on the polished facet of the sample.

13. A sample preparation apparatus comprising:
a chamber adapted for evacuation comprising therein a sample holder adapted to hold a sample comprising a first face bounded by an edge, and the first face comprising a device layer,
and an ion gun arranged to direct an ion beam along an ion beam axis towards said sample,
wherein the sample holder is configurable to position the sample relative to the ion beam such that a first portion of said sample is removable by the ion beam to form a polished facet between said edge and said first face of said sample and such that the ion beam does not impinge onto the exterior of the first face,
characterised in that the sample holder is configured to hold said sample whereby the ion beam axis lies on an ion beam plane oriented at a glancing incident angle from 1° to 30° to a sample plane defined by and parallel to the first face of said sample, and in that the ion beam is arranged to flow from said edge towards said first face, the sample preparation apparatus being configured such that ions of the ion beam cross the plane of the first face from a space originally occupied by the sample, to a space unoccupied by the sample above the first face and therefore would impinge on a back of the first face if not for the presence of the first portion of the sample, removed by the ion beam to form the polished facet.

14. The sample preparation apparatus of claim 13 further comprising a shield positioned between the ion gun and the sample holder to define said first portion of said sample unshielded from the ion beam and a second portion of said sample shielded from the ion beam.

15. The sample preparation apparatus of claim 13 further comprising a means for monitoring the sample removal process wherein the means for monitoring the sample removal process is adapted to provide signals related to the extent of removal of said first portion.

16. The sample preparation apparatus of claim 15 wherein the means for monitoring the sample removal process comprises or is a microscope means arrangeable to monitor the sample during removal of said first portion.

17. The sample preparation apparatus of claim 15 further comprising a control means operably connected to the ion gun and to the means for monitoring the sample removal process and adapted to vary one or more parameters of the ion beam during removal of said first portion in response to the signals related to the extent of removal of the first portion received from the means for monitoring the sample removal process of a control program.

18. The sample preparation apparatus of claim 15 wherein the apparatus comprises a means for varying the ion beam position and/or the ion beam geometry relative to said sample in response to the signals related to the extent of removal of the first portion.

19. The sample preparation apparatus of claim 15 wherein the ion gun comprises a mechanical or electromagnetic adjustment means whereby the position and/or geometry of the ion beam are variable in response to the signals related to the extent of removal of the first portion.

20. The sample preparation apparatus of claim 13 comprising two or more ion guns each arranged to direct an ion beam along a respective ion beam axis towards said sample.

* * * * *